United States Patent [19]

Walton, II

[11] 4,281,457
[45] Aug. 4, 1981

[54] VACUUM-OPERATED CUTTING TOOL AND SYSTEM THEREFOR

[75] Inventor: Richard E. Walton, II, Fallston, Md.

[73] Assignee: Black & Decker Inc., Newark, Del.

[21] Appl. No.: 86,025

[22] Filed: Oct. 17, 1979

[51] Int. Cl.³ .......................... B27B 9/00; B26B 25/00
[52] U.S. Cl. ......................................... 30/124; 30/133
[58] Field of Search ...................... 30/133, 166 R, 124

[56] References Cited

U.S. PATENT DOCUMENTS

| 2,975,517 | 3/1961 | Brittain | 30/133 |
| 3,103,069 | 9/1963 | Gary | 30/133 X |
| 3,138,870 | 6/1964 | Stachon | 30/133 X |
| 3,481,036 | 12/1969 | Slaughter | 30/124 |

*Primary Examiner*—Jimmy C. Peters
*Attorney, Agent, or Firm*—Harold Weinstein; Leonard Bloom; Edward D. Murphy

[57] ABSTRACT

A vacuum-operated cutting tool and system includes a power tool that operates in response to a vacuum induced fluid-flow. The tool includes a housing having an impeller section with an outlet adapted for connection to a vacuum-inducing source and an inlet through which ambient air enters the tool. A rotatably mounted turbine-impeller is located within the impeller section of the housing and is adapted to rotate in response to the vacuum-induced fluid-flow. In the preferred embodiment, a motion converting mechanism is connected between the turbine-impeller and a drive spindle equipped with a circular saw blade. The motion converting mechanism converts the rotary output motion of the turbine-impeller to a rotary oscillating motion so that the saw blade is suited for use in cutting plaster casts. The air inlet of the housing is advantageously located in the cutting zone of the saw blade to entrain and remove debris generated during the cutting operation.

8 Claims, 11 Drawing Figures

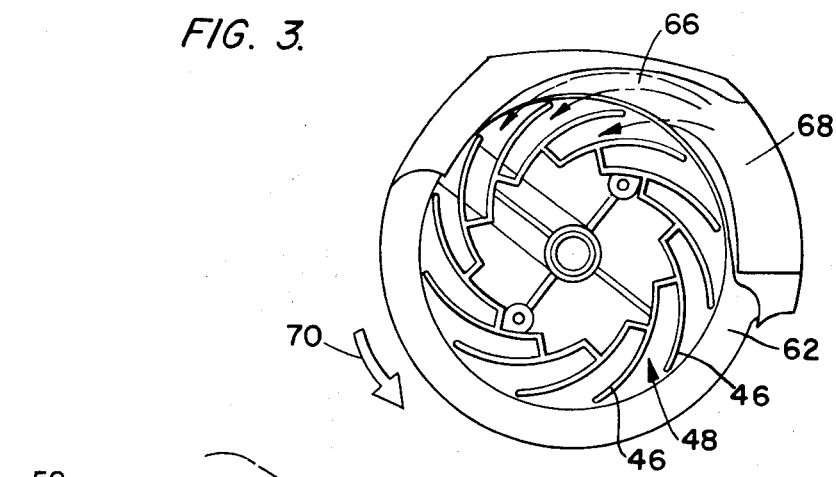
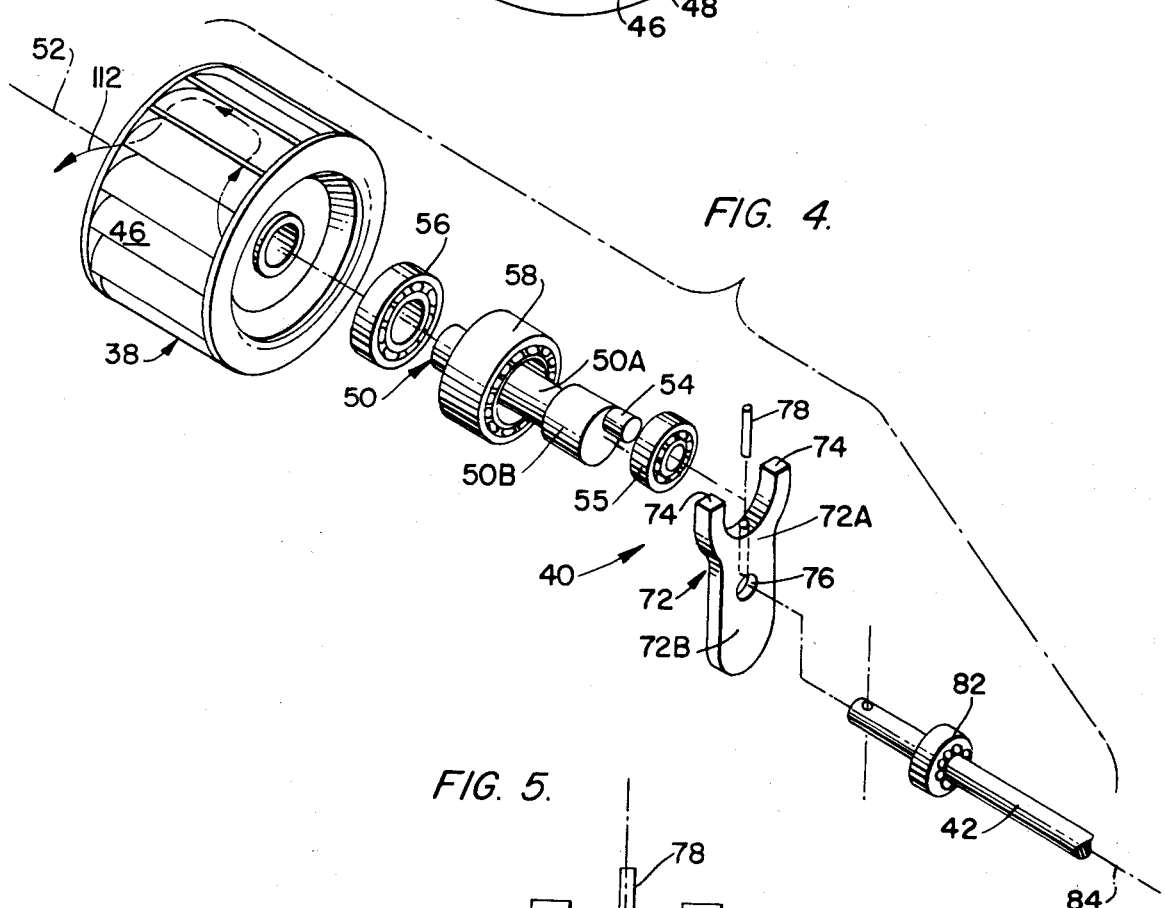
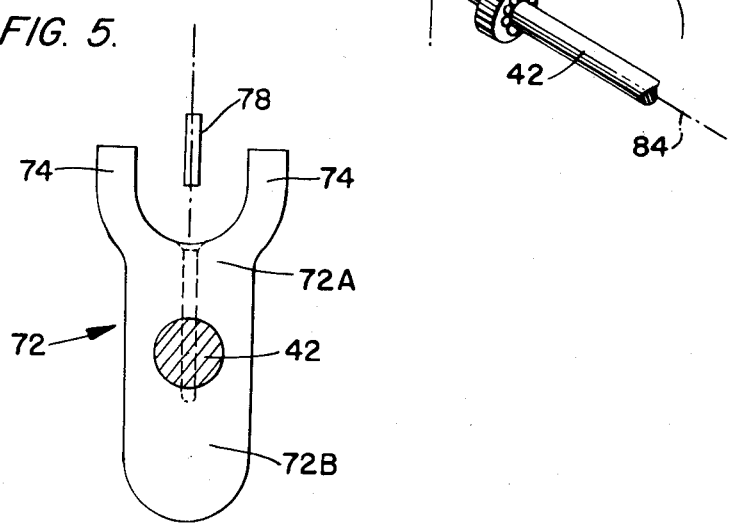

VACUUM-OPERATED CUTTING TOOL AND SYSTEM THEREFOR

Field of the Invention

The present invention relates to a power tool adapted to operate in response to a vacuum-induced fluid flow and, more particularly, to a portable vacuum-powered oscillating circular saw suitable for use as a plaster cast cutter.

BACKGROUND OF THE INVENTION

Portable power tools adapted for use in cutting and removing plaster casts have generally included an electrically powered motor connected to a circular saw blade through a motion converting mechanism that converts the rotary motion of the motor to an oscillating rotary motion. The oscillating nature of the circular blade, as is known in the art, permits the blade to readily cut through a plaster cast without damage to underlying skin or tissue. Typically, these tools have also been provided with a hose connection to a vacuum producing source with the inlet end of the hose positioned in or adjacent to the cutting zone of the blade to entrain and remove the debris generated during the cutting operation.

Since the above-described tool is designed for hand-held operation and manipulation, the electric motor adds weight to the tool and the combined hose and electrical connections limit the maneuverability of the tool. Also, the electric motor generally produces heat energy during use which must be dissipated, and the motor must also be protected or otherwise shielded against the debris generated during a cutting operation.

SUMMARY OF THE INVENTION

In view of the above, it is an object of the present invention, among others, to provide a power tool that operates solely in response to a vacuum-induced fluid flow.

It is another object of the present invention to provide a vacuum-powered rotary cutting tool which is light weight and convenient to manipulate.

It is still another object of the present invention to provide a vacuum-powered circular saw in which the saw is driven by power derived from a turbine wheel that rotates in response to a vacuum-induced fluid flow through the tool housing.

It is a further object of the present invention to provide a vacuum-powered cast cutting saw in which the blade is driven through a motion converting mechanism with power derived from a turbine wheel that is driven in response to a vacuum-induced fluid flow.

It is a still further object of the present invention to provide a vacuum-powered saw cutter in which the power for driving the circular saw blade and a fluid-flow stream for removing the debris generated during the cutting operation are derived from a single vacuum providing source.

A vacuum-operated power tool in accordance with the present invention includes a tool housing having an impeller section that includes a inlet side for drawing ambient air into the tool housing and an outlet side for exhausting the ambient air to a vacuum-inducing source. A rotatably mounted turbine means is located within the impeller section and is adapted to rotate in response to the vacuum-induced fluid flow through the impeller section from the inlet side to the outlet side of the tool. The turbine means is coupled through a motion converting mechanism to a drive shaft that is adapted to releasably retain a cutting tool, such as a circular saw. The motion converting means converts the rotary output motion of the turbine means into a rotary oscillating motion to enable the saw blade to be adapted for cutting plaster casts. The inlet portion of the housing is located adjacent the circular saw cutting zone such that the ambient air drawn into the tool housing entrains and removes debris and other particles generated during the cutting operation. In the preferred embodiment, the motion converting mechanism includes a rotatably mounted shaft connected to the turbine means. The shaft includes an eccentric cam portion that fits between the spaced apart tines of a bifurcated wishbone-type cam follower that is connected to the drive shaft.

A vacuum-operated power tool in accordance with the present invention advantageously provides a lightweight, easily manipulatable tool in which both the power to operate the cutting tool and the air flow to remove the debris generated during the cutting operation are provided by the same vacuum-inducing source.

DESCRIPTION OF THE FIGURES

The above description, as well as the objects, features, and advantages of the present invention will be more fully appreciated by reference to the following detailed description of presently preferred but nonetheless illustrative embodiment in accordance with the present invention, when taken in conjunction with the accompanying drawings wherein:

FIG. 3 is a cross-sectional view of a turbine wheel and a fluid-flow directing nozzle of the power tool illustrated in FIGS. 1 and 2 taken along line 3—3 of FIG. 2;

FIG. 4 is an exploded perspective view of an exemplary drive train for the power tool illustrated in FIGS. 1 and 2 with selected parts omitted for reasons of clarity;

FIG. 5 is a detail view of a cam follower portion of the drive train shown in FIG. 4;

DESCRIPTION OF THE PREFERRED EMBODIMENT

Figure 1:
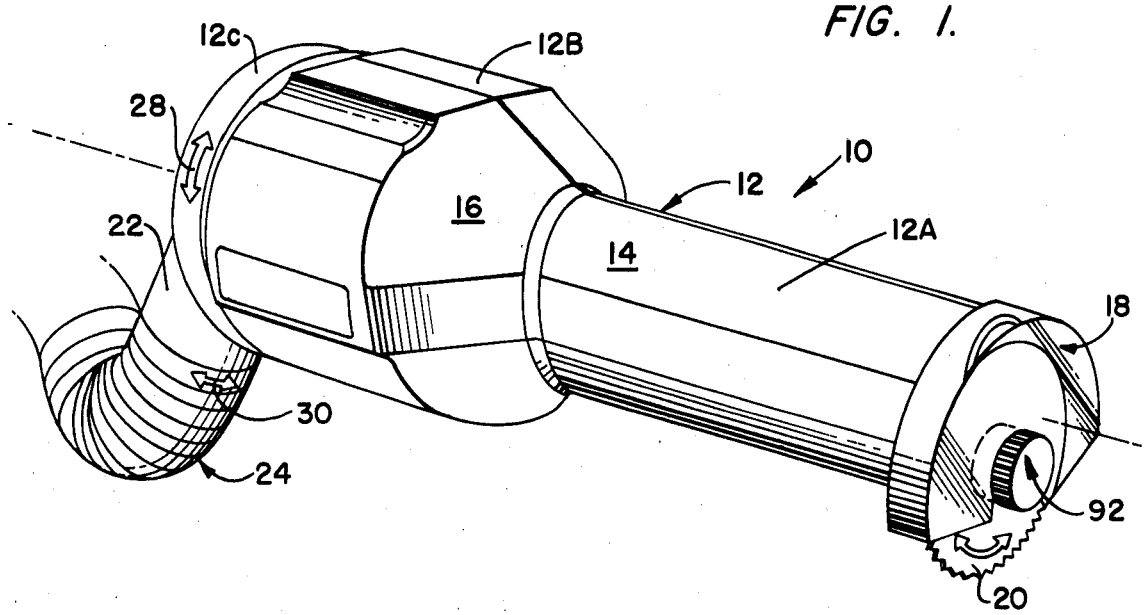
FIG. 1 is a perspective view of a portable vacuum-operated power cutting tool in accordance with the present invention.
Figure 2:
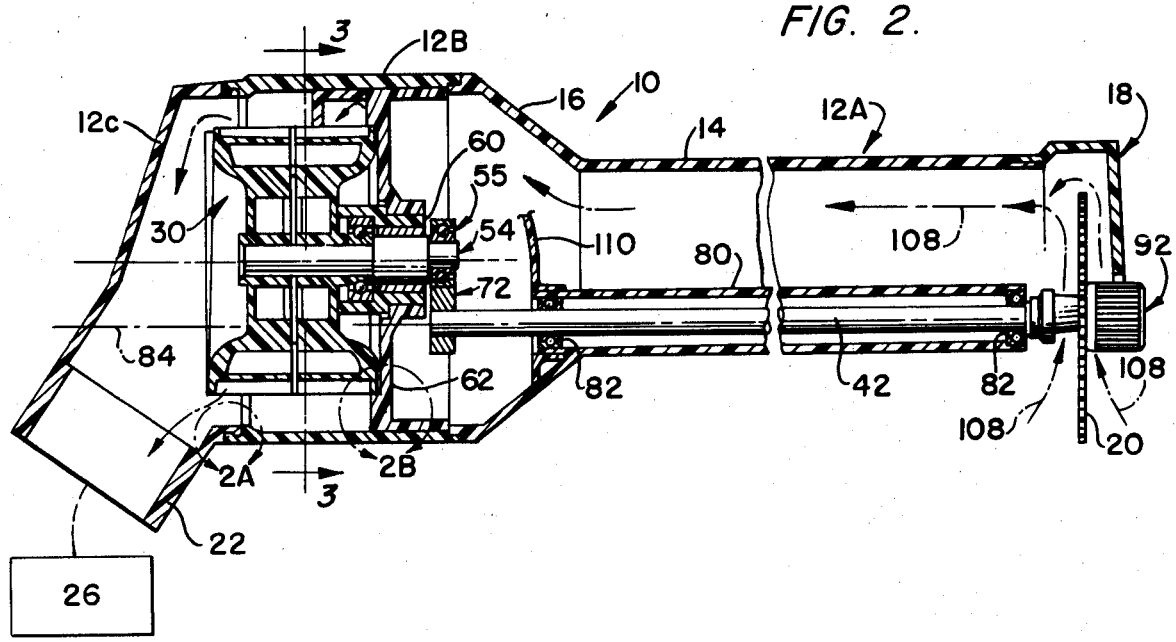
FIG. 2 is a side elevational view, in cross section, of the vacuum-operated power tool shown in FIG. 1.

A vacuum-operated power tool in accordance with the present invention suitable for use as a plaster cast cutting tool or the like is generally referred to in the figures by reference character 10. As shown in FIGS. 1 and 2, the tool 10 includes a housing 12 that includes an inlet section 12A, an impeller section 12B, and an outlet section 12C. The inlet section 12A includes a cylindrically extending surface 14 designed for convenient manual gripping and a conical transistion portion 16 that rigidly joins the inlet section 12A with the impeller section 12B. A shroud 18 is removably connected to the open, remote end of the inlet section 12A and is designed to partially encircle or enclose a circular saw blade 20 and assist in directing inlet air into the open end of the inlet housing 12A across the cutting zone of the blade 20 as described in more detail below. The outlet section 12C includes a cylindrical hose receiving fitting 22 that permits the tool 10 to be connected through a vacuum hose 24 to a vacuum-inducing source such as a vacuum cleaner schematically represented at 26 in FIG. 2. The outlet section 12C of the tool 10 is rotatably mounted to the impeller section 12B such that the outlet section can rotate relative to the inlet section as indicated by the double arrow 28 in FIG. 1. In addition, the vacuum hose 24 is also rotatably mounted relative to the hose receiving fitting 22 as indicated by the double arrow 30 such that the tool 10 may be conveniently manipulated with the outlet section 12C and the vacuum hose 24 conforming to each new attitude and position of the tool 10.

Figure 2A:
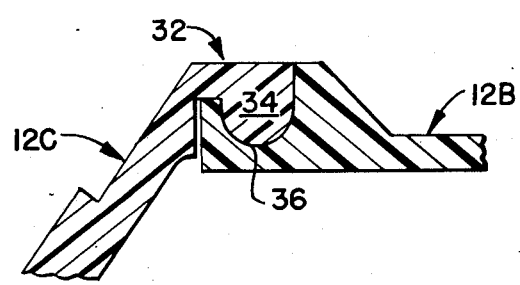
FIG. 2A is an enlarged detail view of a connection joint enclosed by the line 2A in FIG. 2.

In the preferred embodiment, a movable seal structure, as shown in FIG. 2A and generally referred to therein by the reference character 32, is used to effect the rotatable connection between the outlet section 12C and the impeller section 12B. The outlet section 12C includes a radially inward projecting rim 34 having a curved inner surface that is received by and mates with a peripheral, complementary groove 36 formed in the impeller section 12B. A combined sealant/lubricant may be provided on the mating surfaces of the seal 32 to permit low-friction relative rotation and prevent air flow through the seal.

A vacuum-responsive drive system (FIGS. 2-8) is provided internally of the tool housing 12 and is designed to provide motive power for the circular saw blade 20 to cause the blade to oscillate. The drive system includes an impeller or turbine wheel 38, a motion conversion mechanism, generally referred to by the reference character 40, a drive shaft 42, and a chuck assembly 44 (FIGS. 8 and 9) for attaching the saw blade 20 to the drive shaft 42.

Figure 2B:
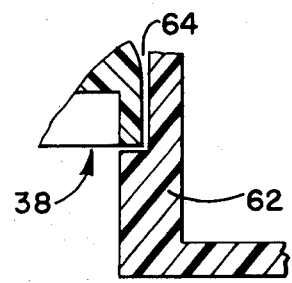
FIG. 2B is an enlarged detail view of a portion of the turbine wheel adjacent a partition wall enclosed by the line 2B in FIG. 2.
Figure 6:
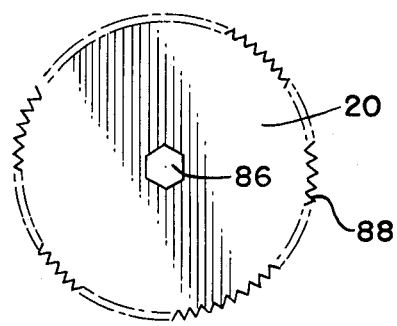
FIG. 6 is a end elevational view of an exemplary circular saw blade for use with the power tool illustrated in FIGS. 1 and 2.

As shown in FIGS. 2, 3, and 4 the turbine wheel 38 includes a plurality of equally spaced blades 46 that define intermediate "buckets" or pockets 48 that extend the full width of the wheel 38. The turbine wheel 38 is secured to a shaft 50 that is rotatably mounted for rotation about a shaft axis 52. The shaft 50 includes a shank portion 50A to which the turbine wheel 38 is secured, an enlarged head portion 50B, and an eccentrically located, axially extending stub shaft 54 that carries a ball bearing 55. The shaft 50 is rotatably mounted in a ball bearing 56 that supports the shank portion 50A of the shaft and a needle bearing 58 that supports the enlarged head portion 50B. The bearings 56 and 58 are carried in a cylindrical bearing cartridge 60 (FIG. 2) which, in turn, is fitted in an appropriately sized bore formed in a partition 62 that separates the impeller section 12B into an upstream side and a downstream side. As shown in FIG. 2B, the partition 62 is counter-bored or recessed on its down-stream side at 64 to accept the right-hand side of the turbine wheel 38.

As shown in FIG. 3, an air-flow directing nozzle 66 is secured to the downstream side of the partition 62 and directs a air-flow from an opening 68 formed in the partition from the upstream side to the turbine wheel 38 to cause the turbine wheel to rotate in the direction of the arrow 70 as described more fully below.

As shown in detail in FIGS. 4 and 5, the motion converting mechanism 40 includes a bifurcated "wishbone"shaped cam follower 72 that includes an upper bifurcated portion 72A having spaced apart tines 74 and a lower counterbalancing portion 72B. The cam follower 72 includes a mounting hole 76 formed intermediate its ends through which the inner end of the drive shaft 42 is inserted. The cam follower 72 is secured to the drive shaft 42 by suitable securing means including the pin 78 as shown in FIG. 4 with the bearing 55 positioned between the tines 74. The drive shaft 42 extends through a drive tube 80 (FIG. 2) formed in the inlet section 12A of the housing 12 and is rotatably carried therein in drive shaft bearings 82 for rotation about its axis 84.

Figure 7:
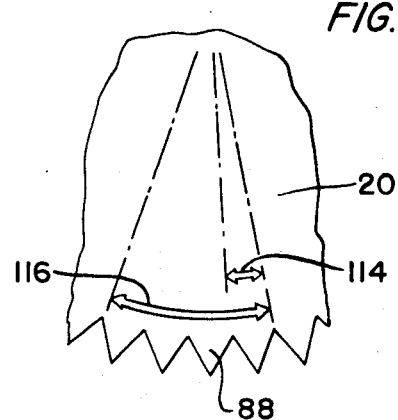
FIG. 7 is an enlarged detailed view of the circular saw blade of FIG. 6 illustrating the amplitude of the oscillating motion of the blade.

A saw blade 20 suitable for use with the present invention is shown in FIG. 7 and includes a centrally located hexagonal mounting hole 86 and a plurality of equi-spaced peripheral teeth 88.

Figure 8:
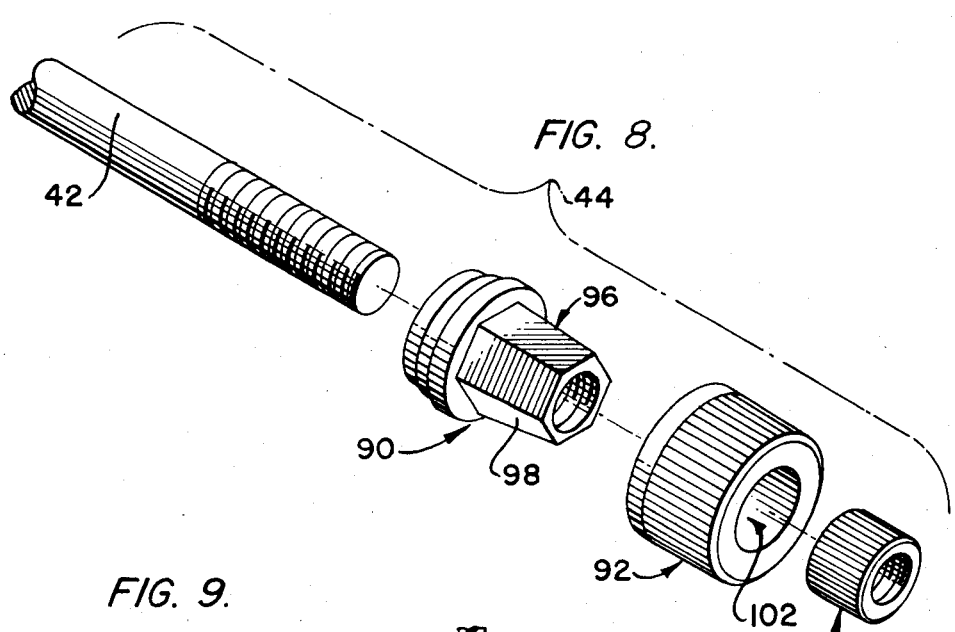
FIG. 8 is an exploded perspective view of a chuck suitable for use with the power tool of FIGS. 1 and 2 for releasably retaining the circular saw blade of FIG. 6.
Figure 9:
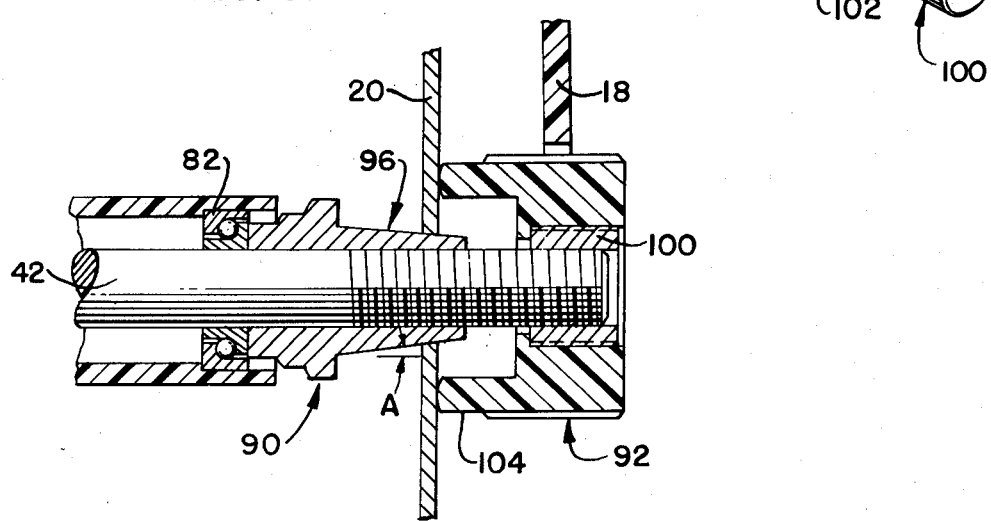
FIG. 9 is a side elevational view, in cross section, of the chuck of FIG. 8 in its assembled state.

The chuck 44 for releasably securing the saw blade 20 to the tool 10 is shown in detail in FIGS. 8 and 9. As shown therein, the chuck 44 is mounted on the outer or remote threaded end of the drive shaft 42 and includes a hollow mandrel 90 and a threaded retaining nut 92. The mandrel 90 includes a hex-shaped nose 96 with the individual flats or sides 98 of the nose tapered in a forward direction at a selected angle e.g., 5° as indicated by the reference letter A in FIG. 9. The mandrel 90 is fitted over the threaded end of the drive shaft 42 and secured in place with a conventional securing means such as a thread locking cement. The retainer nut 92, which is preferably fabricated from a plastic material, includes a threaded insert 100 that is press-fitted into an appropriately shaped counter-bore 102 (FIG. 8) formed in the retainer nut 92. A peripherally extending, axially directed skirt 104 (FIG. 9) is provided on the side of the retainer nut 92 that faces the mandrel 90 to assist in securing a saw blade 20 to the tool 10. The saw blade 20 is mounted on the tool 10 by removing the shroud 18 and then placing the saw blade 20 over the mandrel 90 such that the hex-shaped mounting hole 86 of the saw blade is aligned with the hex-shaped nose 96 of the mandrel 90. Since the hex-shaped nose 96 is tapered, the saw blade 20 positions itself on the mandrel 90 at a point in which a line-to-line fit (that is, a no clearance fit) exists between the saw blade and the mandrel. Thereafter, the retainer nut 92 is threaded onto the remote or distal end of the drive shaft 42 until the skirt 104 contacts the saw blade to secure it in place. In the preferred embodiment, the remote end of the drive shaft 42 and the retainer nut 92 are provided with a thread having a pitch that inhibits unintentional loosening or unthreading of the retainer nut during operation of the tool 10. A preferred thread suitable for this purpose is a 10-40 thread which has a lead angle of less than 3°, which lead angle has been found effective in preventing unintentional unthreading.

In operation, the tool 10 is connected to any suitable vacuum-inducing source such as a hospital vacuum source (schematically represented at 26 in FIG. 2) or connected to the built-in central vacuum system which may be provided in some hospitals and physician offices. The vacuum-inducing source causes a vacuum-induced fluid-flow to be established through the tool 10 from the inlet end to the outlet end. As shown by the flow arrows 108 in FIG. 2, ambient air enters the tool 10 through the open end of the inlet section 12A with the shroud 18 partially encircling the saw blade 20 to cause the inlet air to flow across and traverse the cutting zone of the saw blade 20 as it enters the tool. The air then flows longitudinally along the inlet section 12A and is deflected from the motion converting mechanism 40 by a baffle 110 to thereby protect the motion converting mechanism 40 from the particulate material entrained with the fluid flow. The air enters the impeller section 12B and flows, as shown in FIG. 3, through the opening 68 in the partition 62 and through the nozzle 66 which directs the air flow onto the turbine wheel 38. The nozzle 66 is arranged so that the air enters the turbine pockets 48 defined between the blades 46 and then flows longitudinally rearward along the width of the pockets 48, as shown by the flow arrow 112 in FIG. 4. The air then exits each pocket into the outlet section 12C for removal through the vacuum hose 24 to the vacuum-inducing source 26. The particular flow path indicated by the arrow 112 in FIG. 4 assists in preventing particulate matter from accumulating in the pockets 48 and consequently diminishing the performance of the tool 10. The fluid-flow through the nozzle 66 causes the turbine wheel 38 and its mounting shaft 50 to rotate at approximately 20,000 RPM in the direction of the arrow 70 in FIG. 3. As a consequence of the rotation of the turbine wheel 38, the eccentrically located stub-shaft 54 and the bearing 55 are casued to revolve or orbit around the longitudinal axis 52 of the shaft 50 to cause the wishbone-shaped cam follower 72 to oscillate the drive shaft 42 with the amplitude of the oscillation determined by the eccentricity of the stub-shaft. The lower counter balancing portion 72B of the cam follower 72 assists in minimizing undesirable vibration of the tool 10. The motion converting mechanism 40 is designed to cause the saw blade 20 to oscillate at an amplitude between one and four tooth-pitch as indicated, respectively, by the amplitude arrows 114 and 116 in FIG. 7. This amplitude, as is known in the art, is effective for cutting a plaster cast without causing damage to underlying skin and tissue.

When the oscillating saw blade 20 is applied against a plaster cast using, e.g., a plunge-cut motion, the blade 20 penetrates the cast with the debris generated during the cutting motion entrained by the inlet air as it traverses the blade cutting zone to enter the saw inlet. A tool 10 in accordance with the present invention advantageously provides a light-weight, easily manipulatable cast cutting saw in which the motive power for both the saw and cutting debris removal are provided from a single vacuum-inducing source. Since the electric motor previously employed with prior cast cutting saws is eliminated, the tool is then both lighter in weight and more manipulatable than prior tools and does not undergo the rise in operating temperature that is normally associated with the prior electrically driven tools.

As will be apparent to those skilled in the art, various changes and modifications may be made to the vacuum-powered rotary cutting tool without departing from the spirit and scope of the present invention as defined in the depending claims and their legal equivalent.

What is claimed is:

1. A cast cutting tool for cutting casts and the like using an oscillating saw blade, said tool comprising:
    (a) a housing for supporting a flow of air therethrough from an inlet opening on an inlet side of said housing to an outlet side thereof,
    (b) a turbine means rotatably mounted within said housing for rotation in response to a vacuum-induced air flow therethrough,
    (c) a motion converting means connected to said turbine means for converting the rotary motion of said turbine means to a rotary oscillating motion about an axis of rotation,
    (d) a chuck means connected to said motion converting means through a drive shaft, said chuck means adapted to receive a saw blade thereon, the saw blade caused to oscillate about said axis of rotation in response to rotation of said turbine means,
    (e) said housing having an elongated inlet portion having an external surface thereon for manual gripping, said drive shaft extending through said elongated inlet portion from said motion converting means to said chuck means, the inlet opening located proximate said chuck means, and
    (f) said elongated inlet portion is divided into a drive shaft tunnel through which said drive shaft extends from said motion converting means to said chuck means and an air flow channel.

2. A cast cutting tool for cutting casts and the like using an oscillating saw blade, said tool comprising:
    (a) a housing for supporting a flow of air therethrough from an inlet side to an outlet side, said outlet side having an outlet fitting for connection to a vacuum-inducing source for inducing an air flow through said housing from said inlet to said outlet sides,
    (b) a turbine means rotatably mounted in said housing for rotation in response to said vacuum-induced air flow therethrough,
    (c) a motion converting means connected to said turbine means for converting the rotary motion of said turbine means to a rotary oscillating motion about an axis of rotation,
    (d) chuck means for detachably receiving a saw blade thereon, the saw blade caused to oscillate about said axis of rotation to effect cutting in response to rotation of said turbine means,
    (e) a partition dividing said housing into an upstream side and a downstream side, said partition having an opening formed therethrough so that the air flows from said upstream side through said opening to said turbine means to effect rotation thereof, and
    (f) a nozzle connected to the downstream side of said partition and in registration with said opening therein for directing the air flow from said opening in said partition to said turbine means.

3. The cast cutting tool claimed in claim 2 wherein a surface portion of said partition on the downstream side thereof is recessed to receive a portion of said turbine means therein.

4. A cast cutting tool for cutting casts and the like using an oscillating saw blade, said tool comprising:

(a) a housing means for supporting a flow of air therethrough from an inlet side to an outlet side in response to a vacuum-inducing source, (b) a turbine means rotatably mounted in said housing for rotation about an axis in response to said vacuum induced air flow therethrough, (c) a motion converting means connected to said turbine means for converting the rotary motion of said turbine means to a rotary oscillating motion about an axis of rotation, said motion converting mechanism including a rotatably mounted shaft upon which said turbine means is mounted for rotation therewith, an eccentric cam surface connected to said turbine mounting shaft, and a cam follower that engages said eccentric cam surface and that oscillates in response to rotation of said cam surface, said cam follower connected to a rotatably mounted drive shaft, (d) chuck means connected to said drive shaft for detachably receiving a saw blade of the type having cutting teeth formed on a curvilinear periphery thereof, the saw blade caused to oscillate to effect cutting in response to rotation of said turbine means, (e) said cam follower including a bifurcated fork having spaced apart tines, which tines are positioned on opposite sides of said eccentric cam surface, and (f) said bifurcated fork including a counter balancing portion thereof on the end remote from said tines.

5. The cast cutting tool for cutting casts and the like using an oscillating saw blade, said tool comprising:

(a) a housing means for supporting a flow of air therethrough from an inlet side to an outlet side, (b) a turbine means rotatably mounted in said housing for rotation in response to a vacuum induced air flow therethrough, (c) a motion converting means connected to said turbine means for converting the rotary motion of said turbine means to a rotary oscillating motion, (d) a chuck means connected to said motion converting means for detachably receiving a saw blade thereon, said saw blade caused to oscillate about an axis of rotation in response to rotation of said turbine means to thereby effect cutting, the saw blade of the type having a central aperture and said chuck means including a mandrel upon which the saw blade is mounted, and (e) said mandrel, when viewed in a plane transverse to its longitudinal axis, has a polygonol configuration defined by a plurality of flat mounting surfaces.

6. The cast cutting tool claimed in claim 5 wherein said mounting flats are formed at an angle relative to the longitudinal axis of said mandrel, said flats converging in the direction of a common vertex.

7. The cast cutter claimed in claim 6 wherein the taper angle of said mounting flats is five degrees.

8. The cast cutting tool claimed in claim 5 further comprising:

(a) threaded securing means coupled to said mandrel for securing a saw blade in place on said mandrel, (b) said threaded securing means including an externally threaded shaft extending outwardly of the remote end of said mandrel and a complementary retainer nut for engagement with said threaded shaft to bear against the saw blade to maintain the saw blade in place, and (c) said retainer nut includes an annular, axially extending skirt adapted to contact the saw blade at a diameter less than the outside diameter of the saw blade and greater than the inside diameter of the saw blade.

* * * * *